United States Patent
Du

(10) Patent No.: US 9,629,866 B2
(45) Date of Patent: Apr. 25, 2017

(54) USE OF CORDYCEPIN IN MANUFACTURE OF MEDICAMENTS FOR ANTI-DEPRESSION

(71) Applicant: BEIJING GRAGEN BIOTECHNOLOGY CO. LTD., Beijing (CN)

(72) Inventor: Jing Du, Beijing (CN)

(73) Assignee: BEIJING GRAGEN BIOTECHNOLOGY CO. LTD., Beijing (CN)

( * ) Notice: Subject to any disclaimer, the term of this patent is extended or adjusted under 35 U.S.C. 154(b) by 0 days.

(21) Appl. No.: 14/423,084

(22) PCT Filed: Aug. 12, 2013

(86) PCT No.: PCT/CN2013/081295
§ 371 (c)(1),
(2) Date: Feb. 20, 2015

(87) PCT Pub. No.: WO2014/029285
PCT Pub. Date: Feb. 27, 2014

(65) Prior Publication Data
US 2015/0209380 A1 Jul. 30, 2015

(30) Foreign Application Priority Data
Aug. 23, 2012 (CN) .......................... 2012 1 0302951

(51) Int. Cl.
A61K 31/7076 (2006.01)
A61K 31/55 (2006.01)
A61K 45/06 (2006.01)

(52) U.S. Cl.
CPC .......... *A61K 31/7076* (2013.01); *A61K 31/55* (2013.01); *A61K 45/06* (2013.01)

(58) Field of Classification Search
CPC ..... A61K 31/7076; A61K 31/55; A61K 45/06
See application file for complete search history.

(56) References Cited

U.S. PATENT DOCUMENTS 3,277,077 A * 10/1966 Holly ....................... C07H 5/02
536/119
2008/0293666 A1* 11/2008 Aldrich ................ C07D 209/08
514/47

FOREIGN PATENT DOCUMENTS

CN 101984975 A 3/2011

OTHER PUBLICATIONS entry for depression, Mayo Clinic, http://www.mayoclinic.org/, accessed online on Jun. 23, 2016.*
definition of derivative, Oxford English Dictionary, http://www.oed.com, accessed online on Jan. 11, 2011.*
Nishizawa et al., Biol. Pharm. Bull., 2007, 30(9), p. 1758-1762.*
Shaffer et al., Pschyosomatic Med., 2014, 76(3), p. 190-196, abstract only.*
English machine translation of CN 101984975 A, https://www.google.com/patents/CN101984975A, accessed online on Jun. 23, 2016.*
Einarson et al., Clin. Ther., 1999, 21(2), p. 296-308.*
Troy, D.B. ed., Remington: The Science and Practice of Pharmacy, 2006, 21st ed., p. 1080-1082.*

* cited by examiner

*Primary Examiner* — Jonathan S Lau
(74) *Attorney, Agent, or Firm* — Maschoff Brennan

(57) ABSTRACT

The present invention provides the use of cordycepin or derivatives thereof in manufacture of medicaments for anti-depression, said derivatives mean pharmaceutically acceptable salts, esters of crodycepin or glycosides formed by cordycepin and saccharides.

16 Claims, 1 Drawing Sheet

USE OF CORDYCEPIN IN MANUFACTURE OF MEDICAMENTS FOR ANTI-DEPRESSION

TECHNICAL FIELD

This invention relates to medical field, especially involving the applications of cordycepin in resisting depression, such as preparing the drug for treating depression, or preparing the adjuvant for preventing depression.

BACKGROUND TECHNOLOGY

Depression has become a common and frequently-occurring disease in modern society, whose incidence is still rising. It is featured by emotional distress, waning interest, retardation of thinking, and reduction of words and actions, and patients with major depression may have the ideas of world-weariness or suicide. Such disease will cause pain to patients and their families and loss to the society which are unmatched by many other diseases. According to the report from World Health Organization (WHO), affective disorder has now become the world's fourth-largest disease, and the patients suffering from depression have amounted to 340 million people worldwide. At present, the incidence of depression in China is about 4% and at least 26 million people have depression, causing the total economic burden of RMB 62.2 billion. In America, it is estimated that 17 million people are suffering from depression and 3 million people are attacked by manic depression, making the cost of treating affective disorder reach as high as USD 44 billion a year (USD 43 billion for coronary heart disease). Over the past 40 years of research on affective disorder, its high incidence and mortality are particularly striking; according to report, the suicide rate reaches up to over 10%, and every year 250,000 people commit suicide in China. Currently, the main drug used for treating depression is serotonin reuptake inhibitor (SRI), etc., which however has disadvantages such as slow onset of action, narrow effect spectrum, big side effects, and easy relapse after drug withdrawal. Now, it is in urgent need of more effective drugs and treatment methods with fast onset of action and small side effects in the field of antidepressant drugs.

The used antidepressant drugs so far have many weaknesses, for example, the shortcomings of currently used 3 kinds of antidepressant drugs, namely monoamine oxidase inhibitors, tricyclic antidepressants and heterocyclic antidepressants, mostly include slow onset of action, narrow antidepressant spectrum, relatively large side effects and easy relapse. Therefore, the existing drugs are not ideal, far from satisfying the needs of patients. It is thus indeed imminent to develop new drugs with fast onset of action, broad antidepressant spectrum and less toxic and side effects, which will bring great social and economic benefits to the society as well.

Cordycepin, as the main active ingredient of cordyceps militaris (especially nucleosides), is the first nucleoside antibiotic isolated from the fungus. Cordycepin is a kind of adenosine analogue (3'-deoxyadenosine), whose molecular formula is $C_{10}H_{13}N_5O_3$, molecular weight 251.24, melting point 230° C.~231° C., alkaline, in the form of acicular or flaky crystal. Its molecular structure is shown in FIG. 1.

The medical effects of cordycepin have been reported, among which the effects in such aspects as anti-inflammation, anti-microbial, anti-virus and anti-tumor have been proved by more and more clinical and basic experiments. It is found based on research that, cordycepin can be antagonistic to the generation of NO product, so cordycepin is likely to become a drug for the treatment of disorders caused by inflammation. At the same time, cordycepin can act as a broad-spectrum antibacterial to inhibit the growth of many pathogenic bacteria like *streptococcus, actinobacillus* mallei, *bacillus anthracis*, swine hemorrhagic *bacillus septicaemiae* and *staphylococcus*. Cordycepin also has inhibitory effects on *bacillus subtilis* and skin pathogenic fungus such as microsporum gypseum, microsporon lanosum and sycosis ringworm fungi. In addition, cordycepin has fairly strong antiviral activity. What's more, some other studies have showed that cordycepin can resist herpes virus and inhibit encephalitis virus as well as HIV-I type infection of human immunodeficiency virus. In recent years, researchers have found that cordycepin shows immunomodulatory effects. Besides, cordycepin can promote T lymphocyte transformation, improve the phagocytosis of mononuclear macrophage system, and activate macrophages to produce cytotoxin to directly kill cancer cells. As cordycepin can interfere with the synthesis of RNA and DNA in gene cells, inhibit cancer cell division, be used as the tool to distinguish different RNA polymerases in cells, and possess the special efficacy of repairing gene cells and protecting genetic codes, it can be used as a nucleoside drug. In 2000, American NCI researchers and the professor from School of Medicine of Boston University jointly confirmed based on study that cordycepin has very good curative effects on leukemia.

Among numerous reports of animal experiments or clinical trials above, the curative effect of cordycepin on depression has not yet been reported, and no instance of treating depression by cordycepin is mentioned.

CONTENTS OF THE INVENTION

This invention provides the applications of cordycepin as antidepressant drug and the antidepressant drug prepared by cordycepin. This drug has the advantages such as remarkable antidepressant effects, fast onset of action and small side effects. The technical scheme is as follows:

An application of cordycepin in the preparation of antidepressant drugs is characterized in that cordycepin and/or its derivatives (i.e. the cordycepin salts and esters, or the glycosides synthesized by cordycepin and sugar) is/are used for preparing antidepressant drugs as pharmacodynamic active ingredient(s).

The mentioned antidepressant drug refers to the drug that prevents or treats depression.

The mentioned drug is in forms of tablet, capsule, powder, nanometer powder, solution, suspension, injecta or drip.

As a kind of antidepressant drug, it is characterized in: The pharmacodynamic active ingredient is cordycepin and/or its derivatives (i.e. the cordycepin salts and esters, or the glycosides synthesized by cordycepin and sugar).

The mentioned "antidepressant" refers to preventing or treating depression.

The dosage forms of drug include tablet, capsule, solution, suspension, injecta or drip.

The mentioned drug also includes pharmaceutically acceptable adjuvant.

The mentioned drug also includes the pharmaceutical ingredient that plays a positive role in treating depression together with cordycepin or its derivatives.

The mentioned drug also includes the ingredient that can improve the stability of cordycepin.

The application of the drug mentioned above in treating depression.

Method of treating depression by the drug mentioned above is characterized in: Dosage is 0.5 mg~1000 mg/kg body weight (bw)/day; administration methods are oral, instillation or injection; the subjects are mammals, including human.

The inventor found that cordycepin has obvious antidepressant effects to mammals.

It is found based on experimental research that, its antidepressant effects are obvious, fast and lasting in the animal model; in the mammal mouse model, cordycepin can produce obvious antidepressant effects in a short period of time (90 minutes), which is superior to the traditional antidepressant drug imipramine in rapidity, and its antidepressant effects can be produced continuously. Depression patients generally complain of inflammatory pain symptoms such as headache, stomach pain and back pain. At the same time of resisting depression, cordycepin can also improve the patient's inflammatory symptoms, and kill viruses, bacteria and fungi that can lead to inflammatory symptoms. For many tumor patients who suffer from the complication of depression after chemotherapy and radiotherapy, cordycepin may resist both tumor and depression. So, cordycepin as a small molecule compound can improve the depression patient's various symptoms, including deprementia, pain and inflammation. The currently used antidepressant drugs work very slowly, usually needing a few weeks, thus it is extremely urgent for the medical field to develop antidepressant drugs with fast onset of action. Cordycepin, as the main ingredient of the traditional Chinese medicine cordyceps sinensis, has long been taken as a tonic by human, whose side effects has not yet reported (e.g. in the experiment process, it does not show the shortcomings as conventional antidepressant drugs do, such as calming, induced epilepsy and ataxia. Cordycepin can be extracted from cultured cordyceps militaris. Cordycepin is expected to become a new antidepressant drug with fast onset of action, excellent curative effects, and without toxic and side effects, which is of huge commercial potential and industrial practicability.

The drug screening tests adopted in this invention are: Mice forced swimming and tail suspension tests. They are two kinds of more commonly used animal behavior despairing depression model tests and can ensure the reliability of screening results.

Mice forced swimming test has been used for the screening test of many antidepressant drugs. And most of antidepressant drugs with clinical therapeutic effects have been proved to be able to effectively reduce the immobility time in the forced swimming test. "Immobility" herein refers to that "animals stop struggling in the water, or stay in a floating state, only showing nostrils for breathing with only small body movement to keep the head floating on the water". Before the test, the drugs to be screened are given. The animals in the condition of forced swimming cannot escape from the harsh environment, leading to despairing animal behaviors. This model method is simple and reliable and it has been widely used in the screening and evaluation of antidepressant drugs.

In the mice tail suspension test, mice present the special quiet immobility state without any struggle in the tail suspension state, and antidepressant drugs can obviously shorten the duration of the immobility state. When tested, mice tails are fixed with clips, hanging upside-down. Do not make the mouse tail twist or fold. The time of immobility is recorded. The immobility indicator is "animal has no body movement in addition to breathing". Tail suspension test is very sensitive to a variety of antidepressant drugs, and the interference of temperature and animal movement dysfunction in the swimming test are avoided, so using some rat species to screen antidepressant drugs can effectively verify and supplement the results of forced swimming test.

The application of cordycepin in resisting depression provided in this invention is not limited to that of the cordycepin with the structural formula shown in FIG. 1. It is a conventional experiment skill for technicians in this field to prepare cordycepin salts and esters by cordycepin or prepare glycosides by cordycepin and sugar, therefore, this invention also contains applications of cordycepin salts and esters, or the glycosides synthesized by cordycepin and sugar in resisting depression. The active ingredients of the prepared drugs can be cordycepin, cordycepin salts and esters, or the described glycosides.

The application of cordycepin in resisting depression provided in this invention indicates that, the adjuvant that will not affect the drug efficacy, such as carrier and excipient, can be added into the prepared antidepressant drug based on knowledge of the technician in this field. Since this drug can be taken effectively by oral, injection and subcutaneous embedding, etc., the dosage form can be varied.

The antidepressant drug provided in this invention can also include other ingredients that are used cooperatively with cordycepin or its derivatives, as well as the pharmaceutical ingredients that have positive effects on treatment of depression.

Due to the poor stability of cordycepin, the technicians in this field can add a stabilizing agent. As long as the obtained antidepressant drug does not affect the efficacy of cordycepin, it is in the scope of protection of this invention.

The antidepressant preparation provided in this invention includes two aspects, namely prevention and treatment.

As per Patent Law, this invention also requires protecting the application of cordycepin in resisting and treating depression; in the animal model test, the dose range of antidepressant treatment effects is 0.5 mg-1000 mg/1 kg.

CONCRETE IMPLEMENTATION PLAN

Example 1: Effects of Cordycepin on Animal Depression Model in Tail Suspension Test Laboratory Animal: CD1 mice, male, 25 g~35 g, provided by Beijing Vital River Laboratories (VRL) (License No.: SCXK (Beijing), 2011-0011). Animals were kept in separate cages with free access to water; feed is provided by Laboratory Animal Center, Institute of Genetics and Developmental Biology, Chinese Academy of Sciences; laboratory mice ate ordinary feed.

Experimental Drug: Cordycepin purchased from Shanghai Yuanye Biological Technology Co., Ltd. (Article No.: YY91028; Batch No.: 20120615).

Imipramine hydrochloride used for positive control is purchased from Sigma-Aldrich (Article No.: 17379; Batch No.: 056K1380).

Laboratory Equipment: Rail, tape, Sumsung Intelli-200 m digital camera (Samsung), and JUNSO multifunction timer.

Cordycepin Mother Liquor: Cordycepin was dissolved in a small amount of pure ethanol to get 10 ug/ul solution, which was then diluted with normal saline.

Laboratory Procedures: CD1 male mice, after acclimating for 1 week, were divided into 5 groups, 8 mice for each:

Cordycepin Control Group (normal saline+1.6% ethanol, injected by 0.3 ml/30 gbw);

Low-dose Cordycepin Group (cordycepin dissolved in normal saline+1.6% ethanol, injected by 5 mg/kgbw);

High-dose Cordycepin Group (cordycepin dissolved in normal saline+1.6% ethanol, injected by 12.5 mg/kgbw);

Imipramine Positive Control Group (imipramine dissolved in normal saline, injected by 15 mg/kgbw);

Imipramine Control Group (normal saline, injected by 0.3 ml/30 gbw).

Drugs were delivered at 10 a.m. by intraperitoneal injection, 90 minutes after which tail suspension test statistics started.

In mice tail suspension test, mice tails were stuck to a horizontal rail with tape 2 cm away from the tail tip, making animals upside down, whose heads were about 15 cm from the desktop. After observing for 6 minutes, the accumulative immobility time within the following 4 minutes was recorded. The immobility indicator was "animal has no body movement in addition to breathing".

Statistical Method: The laboratory results were all expressed by "mean value±SE"; two sample means were compared by t test.

Figure 1:
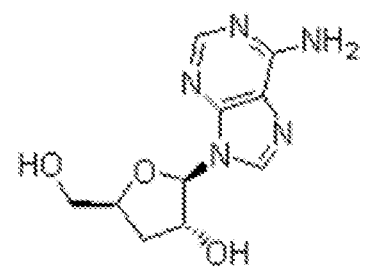
FIG. 1 illustrates the chemical structural formula of cordycepin.
Figure 2:
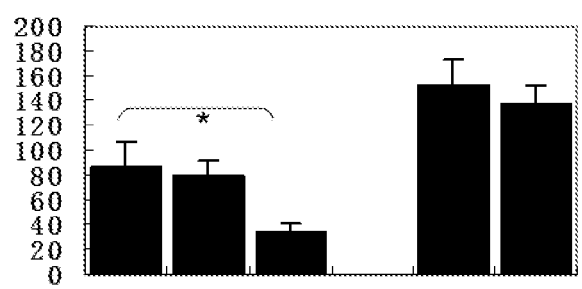
FIG. 2 shows the effects of cordycepin in mice tail suspension test, in which the vertical coordinate represents tail suspension immobility time (S), the horizontal coordinate represents various processing methods (from left to right in turn: Cordycepin control group, low-dose cordycepin, high-dose cordycepin, imipramine control group, imipramine). By comparison, in high-dose group (12.5 mg/kg), CD1 male mice show antidepressant effects only 90 minutes after intraperitoneal injection of cordycepin, which is obviously fast than traditional antidepressant drug imipramine.

Laboratory Results: As shown in FIG. 1, compared with the blank control group, the mice tail suspension immobility time in high-dose cordycepin group can be obviously reduced 90 minutes after injection. The low-dose group has not yet work, showing a dose response. The results indicate that, high-dose cordycepin is able to take effect in a very short period of time to fight against mice's depressive symptoms caused by forced tail suspension; the antidepressant effect of cordycepin occurs earlier than traditional antidepressant drugs, which only needs 1.5 h to be very obvious.

Compared with the blank control group, the mice immobility time in high-dose cordycepin group reduces from 86.43±20.37 s to 33.86±7.46 s ($P<0.05$), decreasing by 60.8%. In low-dose cordycepin group, immobility time shows a reduced trend, which however has not been significantly reduced. Since the solvent is ethanol, the immobility time in cordycepin control group slightly declines. Compared with traditional antidepressant drug imipramine, high-dose cordycepin shows rapid antidepressant effects. At 90th minute after injection, the mice treated by traditional antidepressant drug imipramine (15 mg/kg) are almost the same with those in blank control group, which means that imipramine, with a relatively slow onset of action, has not yet taken effect.

Example 2: Mice Forced Swimming Test

Laboratory Animal: CD1 mice, male, provided by Beijing Vital River Laboratories (VRL) (License No.: SCXK (Beijing), 2011-0011). Animals were kept in separate cages a week before test, with a light and shade cycle of 12 h/12 h, at room temperature 20° C.~22° C., and with free access to water and food. Feed is provided by Laboratory Animal Center, Institute of Genetics and Developmental Biology, Chinese Academy of Sciences.

Experimental Drug: Cordycepin purchased from Shanghai Yuanye Biological Technology Co., Ltd. (Article No.: YY91028; Batch No.: 20120615). Imipramine hydrochloride used for positive control is purchased from Sigma-Aldrich (Article No.: 17379; Batch No.: O56K1380).

Laboratory Instrument: Glass cylinder (20 cm in height and 14 cm in diameter); open box (30 cm in diameter, 20 cm in height, and 16 equal divisions in bottom); thermometer; JUNSO multifunction timer.

Drug preparation is the same as the tail suspension test.

Laboratory Procedures:

Drug Injection in Animals:

CD1 mice, 7 weeks old, 25 g-35 g, were used for test after acclimating for 1 week. Mice were divided into 5 groups randomly, 8 mice for each. They were treated in the same way as Example 1: Drugs were delivered at 10 a.m. by intraperitoneal injection, once a day for 3 days, then forced swimming test started.

Forced swimming test: All CD1 mice in each group were separately and vertically put into the organic glass cylinder (40 cm×14 cm in diameter) with 15 cm-depth and 23° C. water. After recoding a video of each dose group and control group for 6 minutes, the accumulative immobility time within the following 4 minutes was compared between each group. The immobility indicator was that, mice were floating in the water and did not try to climb out of the cylinder, only doing some necessary actions to keep their head on the water surface.

Statistical Analysis Method: The analyst analyzed results in accordance with the unified standards. The laboratory results were all expressed by "mean value±SE"; two sample means were compared by t test.

Figure 3:
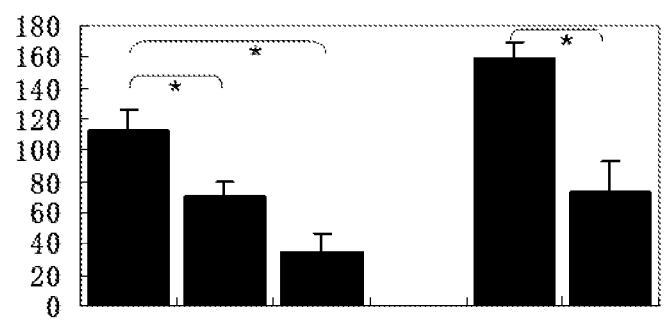
FIG. 3 shows the effects of cordycepin in mice forced swimming test, in which the vertical coordinate represents the immobility time (S), the horizontal coordinate represents various processing methods (from left to right in turn: Cordycepin control group, low-dose cordycepin, high-dose cordycepin, imipramine control group, imipramine). Test results suggest that, CD1 male mice also show antidepressant effects in mice forced swimming test three days after intraperitoneal injection of different doses of cordycepin, and the effects are stronger than the traditional antidepressant drug imipramine. (N=4~8 animals in each group; for *t test, $p<0.05$, **$p<0.01$).

The results suggest that, cordycepin has comparatively strong antidepressant effects. Compared with the blank control group, the immobility time within 4 minutes of forced swimming in high-dose cordycepin group and low-dose cordycepin group is significantly shortened and presented a certain dose dependent; the immobility time in blank control group and high-dose cordycepin group reduces from 111.96±14.58 s to 69.88±10.25 s ($P<0.05$) and 34.94±12.16 s ($P<0.05$) respectively, decreasing by 37.6% and 68.8% severally, as shown in FIG. 3. Compared with traditional antidepressant drug imipramine, high-dose cordycepin has stronger antidepressant effects.

Example 3: Mice Open Field Test to Verify the Central Excitability of Cordycepin Laboratory materials and methods are the same as Example 1 and Example 2.

Considering that the reduced immobility time of animals in classic animal depression models may be due to the central excitability effect of drugs, we conducted a mice open field test to verify the central excitability of cordycepin. Mice were processed 1 d before the open field behavior test. They were kept in the open box with 80 cm in both length and width, 40 cm in height, black wall, 16 equal sections in area, and indoor sound insulation. After the test started, mice were put in the middle of the box, and the time of mice staying in the central 4 sections was taken as a parameter. The measuring time was 1 h/mouse every time. The results indicate that, the time staying in the central 4 sections in high-dose cordycepin group (379.88+95.28 s) and low-dose (399.75+72.25 s) is not distinctly different from that in control group (424.15+82.78 s) (Anova, $p>0.05$, $N=12$). Besides, there is no rising trend, so for cordycepin, the possibility of causing the manic state can be ruled out.

The invention claimed is:

1. An antidepressant drug composition, comprising:
a therapeutically effective amount of a pharmacodynamic active ingredient selected from cordycepin, cordycepin salts, cordycepin esters and cordycepin glycosides synthesized from cordycepin and sugar, wherein the therapeutically effective amount is sufficient to treat depression in a subject, wherein the pharmacodynamic active ingredient includes a cordycepin glycoside.

2. The drug composition of claim 1, having a dosage form comprises a tablet, capsule, powder, nanometer powder, solution, suspension, injecta or drip.

3. The drug composition of claim 1, further comprising a pharmaceutically acceptable adjuvant.

4. The drug composition of claim 1, further comprising a pharmaceutical ingredient that plays a positive role in treating depression together with the cordycepin or its derivatives.

5. The drug composition according to claim 4, wherein the pharmaceutical ingredient is imipramine.

6. The drug composition of claim 1, further comprising an ingredient that improves stability of the cordycepin.

7. The drug composition according to claim 1, further comprising ethanol.

8. The drug composition according to claim 7, wherein the cordycepin is present in the ethanol at 10 micrograms/microliters.

9. The drug composition according to claim 7, further comprising a saline solution having pharmacodynamic active ingredient and ethanol.

10. The drug composition according to claim 1, further comprising further comprising imipramine or ethanol.

11. The drug composition according to claim 1, wherein the pharmacodynamic active ingredient includes a cordycepin.

12. The drug composition according to claim 1, wherein the pharmacodynamic active ingredient includes a cordycepin salt.

13. The drug composition according to claim 1, wherein the pharmacodynamic active ingredient includes a cordycepin ester.

14. An antidepressant drug composition, comprising:
a therapeutically effective amount of a cordycepin ester and cordycepin glycoside, wherein the therapeutically effective amount is sufficient to treat depression in a subject.

15. The drug composition according to claim 14, further comprising imipramine or ethanol.

16. An antidepressant drug composition, comprising:
a therapeutically effective amount of a cordycepin glycosides synthesized from cordycepin and sugar, wherein the therapeutically effective amount is sufficient to treat depression in a subject.

* * * * *